United States Patent [19]

Edwards

[11] Patent Number: 5,800,379

[45] Date of Patent: Sep. 1, 1998

[54] METHOD FOR ABLATING INTERIOR SECTIONS OF THE TONGUE

[75] Inventor: Stuart D. Edwards, Portola Valley, Calif.

[73] Assignee: Sommus Medical Technologies, Inc., Sunnyvale, Calif.

[21] Appl. No.: 695,796

[22] Filed: Aug. 12, 1996

Related U.S. Application Data

[63] Continuation-in-part of Ser. No. 651,800, May 22, 1996, which is a continuation-in-part of Ser. No. 642,053, May 3, 1996, which is a continuation-in-part of Ser. No. 606,195, Feb. 23, 1996, Pat. No. 5,707,349.

[51] Int. Cl.$^6$ ................................................. A61B 17/20
[52] U.S. Cl. ................................................. 604/22
[58] Field of Search ..................... 604/20–22, 101, 604/264; 606/2–4, 6, 7, 10; 128/395; 607/1, 2

[56] References Cited

U.S. PATENT DOCUMENTS

| | | | |
|---|---|---|---|
| 3,901,241 | 8/1975 | Allen | 128/303.1 |
| 4,011,872 | 3/1977 | Komiya | 128/303.14 |
| 4,411,266 | 10/1983 | Cosman | 128/303.18 |
| 4,423,812 | 1/1984 | Sato | 206/387 |
| 4,532,924 | 8/1985 | Auth et al. | 128/303.17 |
| 4,565,200 | 1/1986 | Cosman | 128/642 |
| 4,901,737 | 2/1990 | Tonne | 128/848 |
| 4,906,203 | 3/1990 | Margrave et al. | 439/188 |
| 4,907,589 | 3/1990 | Cosman | 606/34 |
| 4,947,842 | 8/1990 | Marchosky et al. | 128/401 |
| 4,966,597 | 10/1990 | Cosman | 606/50 |
| 4,976,711 | 12/1990 | Parins et al. | 606/48 |
| 5,046,512 | 9/1991 | Murchie | 128/848 |
| 5,057,107 | 10/1991 | Parins et al. | 606/48 |
| 5,078,717 | 1/1992 | Parins et al. | 606/48 |
| 5,083,565 | 1/1992 | Parins | 128/642 |
| 5,094,233 | 3/1992 | Brennan | 602/6 |

(List continued on next page.)

FOREIGN PATENT DOCUMENTS

| | | |
|---|---|---|
| WO 92/10142 | 6/1992 | WIPO . |
| WO 93/08755 | 5/1993 | WIPO . |
| 94 10925 A | 5/1994 | WIPO . |
| 95 18575 A | 7/1995 | WIPO . |
| WO 96/29946 | 10/1996 | WIPO . |

OTHER PUBLICATIONS

Kaneko, et al., *Physiological Laryngeal Pacemaker*, May 1985, Trans Am Soc Artif Intern Organs, vol. XXXI, pp. 293–296.

Mugica, et al., *Direct Diaphragm Stimulation*, Jan. 1987, Pace, vol. 10, pp. 252–256.

Mugica, et al., Neurostimulation: An Overview, Chapter 21, *Preliminary Test of a Muscular Diaphragm Pacing System on Human Patients*, 1985, pp. 263–279.

Nochomovitz, et al., *Electrical Activation of the Diaphragm*, Jun. 1988, Clinics in Chest Medicine, vol. 9 No. 2, pp. 349–358.

Prior, et al., *Treatment of Menorrhagia by Radiofrequency Heating*, 1991, Int. J. Hyperthermia, vol. 7, pp. 213–220.

Rice, et al., Endoscopic Paranasal Sinus Surgery, Chapters 5, *Functional Endoscopic Paranasal Sinus Surgery, The Technique of Messerklinger*, Raven Press, 1988, pp. 75–104.

Rice et al., Endoscopic Paranasal Sinus Surgery, Chapters 6, *Total Endoscopic Sphenoethmoidectomy, The Technique of Wigand*, Raven Press, 1988 pp. 105–125.

*Primary Examiner*—Manuel Mendez
*Attorney, Agent, or Firm*—Wilson, Sonsini, Goodrich & Rosati

[57] ABSTRACT

A method for reducing a volume of a tongue provides an ablative agent source. The ablative agent source is coupled to an ablative agent delivery device. At least a portion of the ablative agent delivery device is advanced into an interior of the tongue. A sufficient amount of an ablative agent is delivered from the ablative agent delivery device into the interior of the tongue to debulk a section of the tongue without damaging a hypoglossal nerve. Thereafter, the ablative agent delivery device is retracted from the interior of the tongue.

20 Claims, 17 Drawing Sheets

U.S. PATENT DOCUMENTS

| | | | |
|---|---|---|---|
| 5,100,423 | 3/1992 | Fearnot | 606/159 |
| 5,122,137 | 6/1992 | Lennox | 606/40 |
| 5,125,928 | 6/1992 | Parins et al. | 606/48 |
| 5,190,541 | 3/1993 | Abele et al. | 606/46 |
| 5,197,963 | 3/1993 | Parins | 606/46 |
| 5,197,964 | 3/1993 | Parins | 606/48 |
| 5,215,103 | 6/1993 | Desai | 128/784 |
| 5,257,451 | 11/1993 | Edwards et al. | 29/825 |
| 5,275,162 | 1/1994 | Edwards et al. | 128/642 |
| 5,277,201 | 1/1994 | Stern | 607/98 |
| 5,281,217 | 1/1994 | Edwards et al. | 606/41 |
| 5,281,218 | 1/1994 | Imran | 606/41 |
| 5,290,286 | 3/1994 | Parins | 606/50 |
| 5,293,869 | 3/1994 | Edwards et al. | 128/642 |
| 5,309,910 | 5/1994 | Edwards et al. | 128/642 |
| 5,313,943 | 5/1994 | Houser et al. | 128/642 |
| 5,314,466 | 5/1994 | Stern et al. | 607/156 |
| 5,328,467 | 7/1994 | Edwards et al. | 604/95 |
| 5,348,554 | 9/1994 | Imran et al. | 606/41 |
| 5,363,861 | 11/1994 | Edwards et al. | 128/772 |
| 5,365,926 | 11/1994 | Desai | 128/642 |
| 5,366,490 | 11/1994 | Edwards et al. | 607/99 |
| 5,368,592 | 11/1994 | Stern et al. | 606/33 |
| 5,370,675 | 12/1994 | Edwards et al. | 607/101 |
| 5,370,678 | 12/1994 | Edwards et al. | 607/101 |
| 5,383,876 | 1/1995 | Nardella | 606/49 |
| 5,383,917 | 1/1995 | Desai | 607/702 |
| 5,385,544 | 1/1995 | Edwards et al. | 604/22 |
| 5,397,339 | 3/1995 | Desai | 687/116 |
| 5,398,683 | 3/1995 | Edwards et al. | 128/642 |
| 5,403,311 | 4/1995 | Abele et al. | 606/49 |
| 5,409,453 | 4/1995 | Lundquist et al. | 604/22 |
| 5,421,819 | 6/1995 | Edwards et al. | 604/22 |
| 5,423,808 | 6/1995 | Edwards et al. | 606/34 |
| 5,423,811 | 6/1995 | Imran et al. | 606/41 |
| 5,433,739 | 7/1995 | Sluijter et al. | 607/99 |
| 5,435,805 | 7/1995 | Edwards et al. | 604/22 |
| 5,456,662 | 10/1995 | Edwards et al. | 604/22 |
| 5,456,682 | 10/1995 | Edwards et al. | 606/31 |
| 5,458,596 | 10/1995 | Lax et al. | 606/31 |
| 5,458,597 | 10/1995 | Edwards et al. | 606/41 |
| 5,470,308 | 11/1995 | Edwards et al. | 604/22 |
| 5,471,982 | 12/1995 | Edwards et al. | 128/642 |
| 5,472,441 | 12/1995 | Edwards et al. | 606/41 |
| 5,484,400 | 1/1996 | Edwards et al. | 604/22 |
| 5,486,161 | 1/1996 | Lax et al. | 604/22 |
| 5,505,730 | 4/1996 | Edwards | 606/41 |
| 5,507,743 | 4/1996 | Edwards et al. | 606/41 |
| 5,509,419 | 4/1996 | Edwards et al. | 128/642 |
| 5,514,130 | 5/1996 | Baker | 606/41 |
| 5,514,131 | 5/1996 | Edwards et al. | 606/45 |
| 5,520,684 | 5/1996 | Imran | 606/41 |
| 5,531,676 | 7/1996 | Edwards et al. | 604/22 |
| 5,531,677 | 7/1996 | Lundquist et al. | 604/22 |
| 5,536,240 | 7/1996 | Edwards et al. | 604/22 |
| 5,536,267 | 7/1996 | Edwards et al. | 606/41 |
| 5,540,655 | 7/1996 | Edwards et al. | 604/22 |
| 5,542,915 | 8/1996 | Edwards et al. | 604/22 |
| 5,542,916 | 8/1996 | Hirsch et al. | 604/22 |
| 5,545,161 | 8/1996 | Imran | 606/41 |
| 5,545,171 | 8/1996 | Sharkey et al. | 606/148 |
| 5,545,193 | 8/1996 | Fleischman et al. | 607/99 |
| 5,549,108 | 8/1996 | Edwards et al. | 128/642 |
| 5,549,644 | 8/1996 | Lundquist et al. | 604/22 |
| 5,554,110 | 9/1996 | Edwards et al. | 604/22 |
| 5,556,377 | 9/1996 | Rosen et al. | 604/22 |
| 5,558,672 | 9/1996 | Edwards et al. | 606/41 |
| 5,558,673 | 9/1996 | Edwards et al. | 606/41 |

Average Shrinkage in Z Direction = 20%

METHOD FOR ABLATING INTERIOR SECTIONS OF THE TONGUE

CROSS-REFERENCE TO RELATED APPLICATIONS

This application is a continuation-in-part of U.S. patent application Ser. No. 08/651,800, entitled "Method and Apparatus for Treatment of Air Way Obstructions", filed May 22, 1996, and still pending, which is a continuation-in-part application of allowed U.S. patent application Ser. No. 08/642,053, entitled "Method for Treatment of Airway Obstructions", filed May 3, 1996, which is a continuation-in-part application of U.S. patent application Ser. No. 08/606,195, filed Feb. 23, 1996, entitled "Method for Treatment of Airway Obstructions", now U.S. Pat. No. 5,707,349 which cross-references U.S. patent application Ser. No. 08/516,781 filed Aug. 18, 1995, entitled "Ablation Apparatus and System for Removal of Soft Palate Tissue", now U.S. Pat. No. 5,674,191 having named inventors Stuart D. Edwards, Edward J. Gough and David L. Douglass, which is a continuation-in-part of U.S. application Ser. No. 08/239,658, filed May 9, 1994, now U.S. Pat. No. 5,456,662 entitled "Method for Reducing Snoring by RF Ablation of the Uvula", all incorporated by reference herein.

BACKGROUND OF THE INVENTION

1. Field of the Invention

This invention relates to a method for the treatment of air way obstructions, and more particularly to a method for ablating selected tissue sites in an interior of the tongue without damaging the hypoglossal nerve using ablation energy and/or an ablative agent.

2. Description of Related Art

Sleep-apnea syndrome is a medical condition characterized by daytime hypersomnomulence, morning arm aches, intellectual deterioration, cardiac arrhythmias, snoring and thrashing during sleep. It is caused by frequent episodes of apnea during the patient's sleep. The syndrome is classically subdivided into two types. One type, termed "central sleep apnea syndrome", is characterized by repeated loss of respiratory effort. The second type, termed obstructive sleep apnea syndrome, is characterized by repeated apneic episodes during sleep resulting from obstruction of the patient's upper airway or that portion of the patient's respiratory tract which is cephalad to, and does not include, the larynx.

Treatment thus far includes various medical, surgical and physical measures. Medical measures include the use of medications such as protriptyline, medroxyprogesterone, acetazolamide, theophylline, nicotine and other medications in addition to avoidance of central nervous system depressants such as sedatives or alcohol. The medical measures above are sometimes helpful but are rarely completely effective. Further, the medications frequently have undesirable side effects.

Surgical interventions have included uvulopalatopharyngoplasty, tonsillectomy, surgery to correct severe retrognathia and tracheostomy. In one procedure the jaw is dislodged and pulled forward, in order to gain access to the base of the tongue. These procedures may be effective but the risk of surgery in these patients can be prohibitive and the procedures are often unacceptable to the patients.

Physical measures have included weight loss, nasopharyngeal airways, nasal CPAP and various tongue retaining devices used nocturnally. These measures may be partially effective but are cumbersome, uncomfortable and patients often will not continue to use these for prolonged periods of time. Weight loss may be effective but is rarely achieved by these patients.

In patients with central sleep apnea syndrome, phrenic nerve or diaphragmatic pacing has been used. Phrenic nerve or diaphragmatic pacing includes the use of electrical stimulation to regulate and control the patient's diaphragm which is innervated bilaterally by the phrenic nerves to assist or support ventilation. This pacing is disclosed in *Direct Diaphragm Stimulation* by J. Mugica et al. PACE vol. 10 January–February 1987, Part II, *Preliminary Test of a Muscular Diaphragm Pacing System on Human Patients* by J. Mugica et al. from Neurostimulation: An Overview 1985 pp. 263–279 and *Electrical Activation of Respiration* by Nochomovitez IEEE Eng. in Medicine and Biology; June, 1993.

However, it was found that many of these patients also have some degree of obstructive sleep apnea which worsens when the inspiratory force is augmented by the pacer. The ventilation induced by the activation of the diaphragm also collapses the upper airway upon inspiration and draws the patient's tongue inferiorly down the throat choking the patient. These patients then require tracheostomies for adequate treatment.

A physiological laryngeal pacemaker as described in *Physiological Laryngeal Pacemaker* by F. Kaneko et al. from Trans Am Soc Artif Intern Organs 1985 senses volume displaced by the lungs and stimulates the appropriate nerve to open the patient's glottis to treat dyspnea. This apparatus is not effective for treatment of sleep apnea. The apparatus produces a signal proportional in the displaced air volume of the lungs and thereby the signal produced is too late to be used as an indicator for the treatment of sleep apnea. There is often no displaced air volume in sleep apnea due to obstruction.

One measure that is effective in obstructive sleep apnea is tracheostomy. However, this surgical intervention carries considerable morbidity and is aesthetically unacceptable to many patients. Other surgical procedures include pulling the tongue as forward as possible and surgically cutting and removing sections of the tongue and other structures which can close off the upper airway passage.

A need exists for a method to treat obstructive sleep apnea without major surgical intervention. A further need exists for a method to ablate selected interior sections of the tongue without damaging the hypoglossal nerve with the use of ablative energy and/or an ablative agent.

SUMMARY OF THE INVENTION

Accordingly, an object of the invention is to provide a method to reduce a volume of a selected site in an interior of the tongue without damaging the hypoglossal nerve.

Another object of the invention is to provide a method for ablating selected sections of the interior of the interior of the tongue without damaging the hypoglossal nerve by the delivery of ablation energy or an ablative agent to the selected tissue site.

These and other objects of the invention are achieved in a method for reducing a volume of a tongue. An ablation apparatus is provided that includes a source of ablation energy and an ablation energy delivery device. At least a portion of the ablation energy delivery device is advanced into an interior of the tongue. A sufficient amount of energy is delivered from the energy delivery device into the interior of the tongue to debulk a section of the tongue without damaging a hypoglossal nerve. Thereafter, the ablation energy delivery device is retracted from the interior of the tongue.

In another embodiment, an ablative agent source is provided. The ablative agent source is coupled to an ablative agent delivery device. At least a portion of the ablative agent delivery device is advanced into an interior of the tongue. A sufficient amount of an ablative agent is delivered from the ablative agent delivery device into the interior of the tongue to debulk a section of the tongue without damaging a hypoglossal nerve. Thereafter, the ablative agent delivery device is retracted from the interior of the tongue.

DETAILED DEFSCRIPTION

Figure 1:
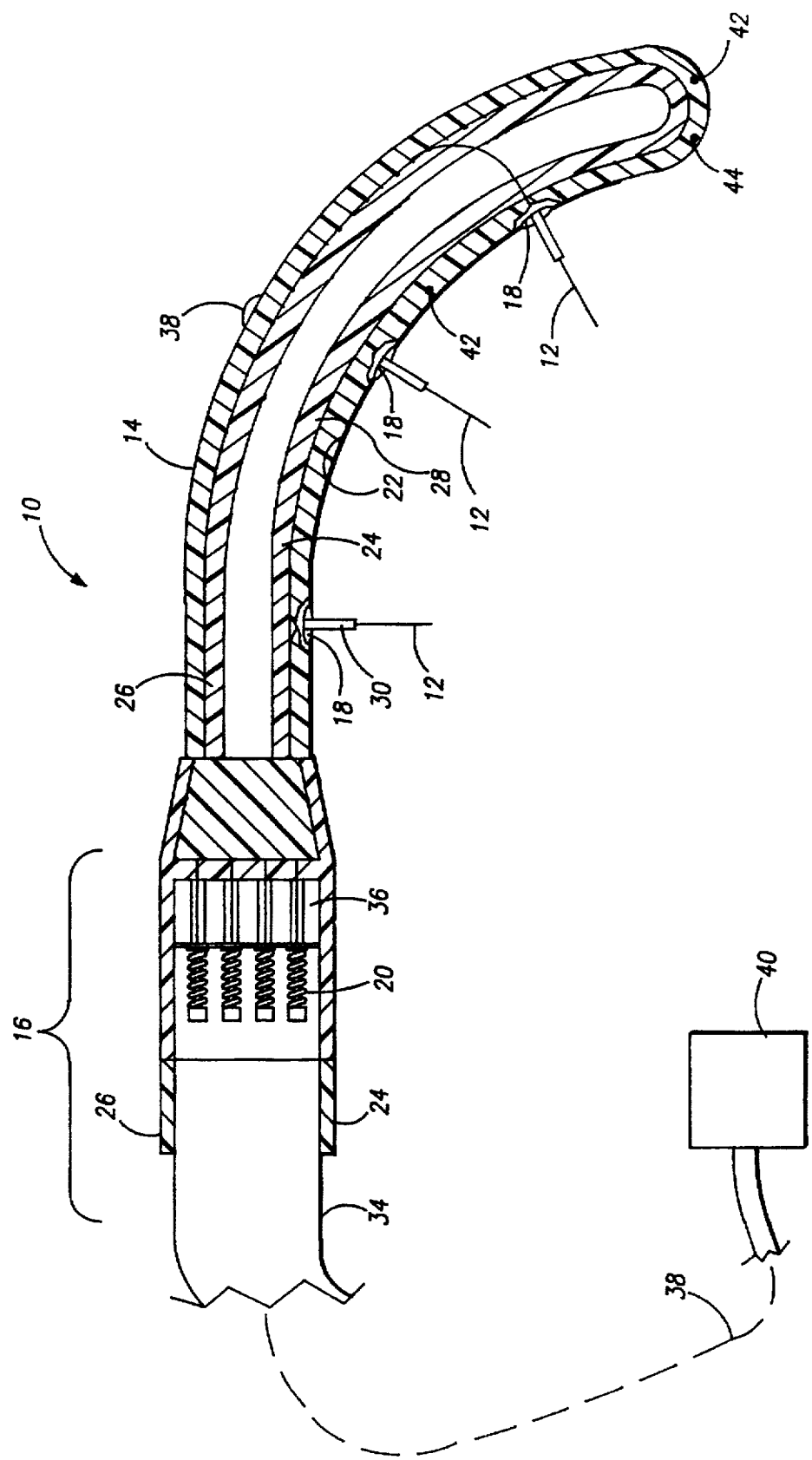
FIG. 1 is a cross-sectional view of an debulking apparatus used with the present invention.
Figure 2:
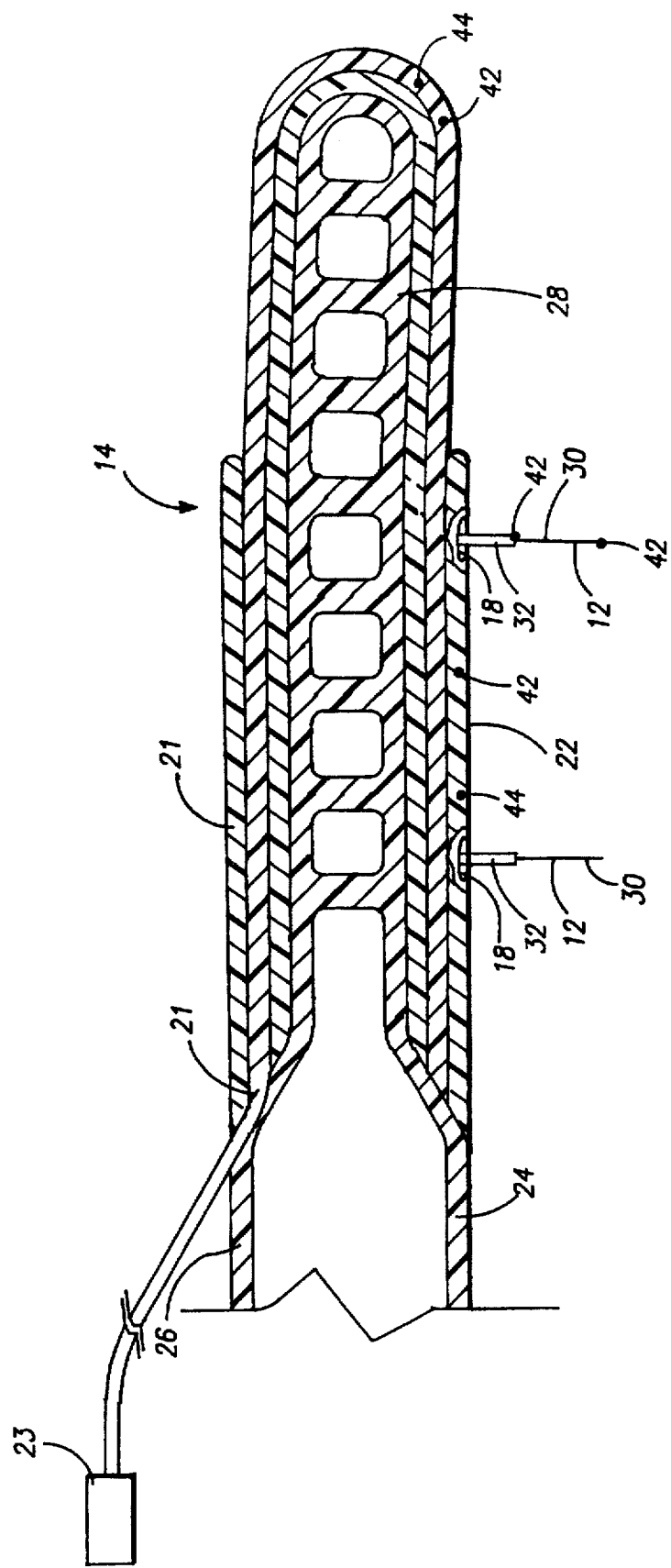
FIG. 2 is cross-sectional view illustrating the catheter and connector of the debunking apparatus shown in FIG. 1.

Referring to FIGS. 1 and 2, a debunking apparatus 10, creating controlled cell necrosis and a reduction of a volume of a selected tissue site including but not limited to the tongue, lingual tonsils, and/or soft palate tissue, including but not limited to the uvula, is illustrated. Debulking apparatus 10 can be positioned so that one or more ablation source delivery devices 12, including but not limited to devices that deliver ablation energy and/or an ablative agent with chemical ablation with any number of different compositions and mixtures to create an ablation, alcohol ablation, diode laser ablation, laser fiber (defused) ablation, chemotherapy coupled with ablation, microwave (915 MHz and 2.45 GHz), ultrasound, thermal ablation or cyro ablation using a hot or very cold solution, solid or gas delivered by infusion such as through a needle, and RF at all relevant frequencies, deliver the ablation energy and/or ablative agent to a selected tissue site and create a desired ablation. Each ablation source delivery source 12 is introduced into an interior of the tongue through a surface of the tongue. Debulking apparatus 10 may include traumatic intubation with or without visualization, provide for the delivery of oxygen or anesthetics, and can be capable of suctioning blood or other secretions. It will be appreciated that debulking apparatus 10 is used to treat a variety of different obstructions in the body where passage of gas is restricted. One embodiment is the treatment of sleep apnea using ablation source delivery device 12 to ablate (create cell necrosis) at selected portions of the tongue, lingual tonsils and/or adenoids by the use of a variety of different energy sources including but not limited to resistive heating, RF, microwave, ultrasound and liquid thermal jet. The preferred energy source is an RF source. In this regard, debulking apparatus 10 can be used to ablate targeted masses including but not limited to the tongue, tonsils, turbinates, soft palate tissues, hard tissue and mucosal tissue. In one embodiment, debulking apparatus 10 is used to ablate an interior region of the tongue, causing it to become debulked in order to increase the cross-sectional area of the airway passage. A disinfectant medium introduction member introduces a disinfectant medium in the oral cavity in order to reduce infection of the ablated body member.

Prior to debulking the tongue, a presurgical evaluation may be performed including a physical examination, fiber optic pharyngoscopy, cephalometric analysis and polygraphic monitoring. The physical examination emphasizes the evaluation of the head and neck. It also includes a close examination of the nasal cavity to identify obstructing deformities of the septum and turbinate; oropharyngeal obstruction from a long, redundant soft palate or hypertrophic tonsils; and hypopharyngeal obstruction from a prominent base of the tongue.

Debulking apparatus 10 includes a catheter 14, an optional handle 16 and one or more ablation source delivery device 12 extending from different ports 18 formed along a longitudinal surface of catheter 14, or from a distal portion of ablation source delivery device 12. Catheter 14 can be a handpiece. An ablation source delivery device advancement device 20 may be provided. Ablation source delivery device advancement device 20 can include guide tracks or tubes 23 positioned in the interior of catheter 14. Ablation source delivery device 12 may be positioned in guide tracks 23 and advanced from the guide tracks into the interior of the tongue. Cabling is coupled to ablation source delivery device 12.

Controlled volumetric reduction of the tongue, under feedback control is used to achieve an effective opening in the airway passage. A variety of different pain killing medicaments, including but not limited to Xylocaine, may be used. A digital ultrasonic measurement system can be used. The ultrasound measurement quantifies biological shape changes, provides ultrasonic transmission and reception, uses piezoelectric transducers (crystals) and provides time of flight data.

A disinfectant medium introduction member 21 may be included and introduced into the oral cavity. Disinfectant medium introduction member 21 can be introduced before, after or during the introduction of debulking apparatus 10 into the oral cavity. Additionally, disinfectant medium introduction member 21 can be removed at the same time or at a different time that debunking apparatus 10 is removed from the oral cavity. Disinfectant medium introduction member 21 can be included in debulking apparatus 10, in an interior of catheter 14 or at an exterior of catheter 14, and may be an introducer with a lumen configured to introduce a disinfectant agent from a disinfectant agent source 23 into all or a selected portion of the oral cavity. Disinfectant medium introduction member 21 can be capable of movement within the oral cavity in order to provide for disinfection of all or only a portion of the oral cavity. For purposes of this disclosure, the oral cavity is that body internal environment where infectious germs may be introduced into the ablated tongue, soft tissue structure, and the like. Disinfectant medium introduction member 21 may be slideably positioned in catheter 14 or at its exterior. Alternatively, disinfectant medium introduction member 21 can be an optical fiber coupled to a light energy source, including but not limited to a UV source 25. The optical fiber can also be slideably be positioned in the oral cavity. The optical fiber is configured to provide for the selective disinfection of all or only a portion of the oral cavity and can have a variety of different distal ends to achieve this purpose.

Suitable disinfectant agents include but are not limited to Peridex, an oral rinse containing 0.12% chlorhexidine glucinate (1,1'-hexanethylenebis[5-(p-chlorophenyl) biganide}di-D-gluconate in a base containing water, 11.6% alcohol, glycerin, PEG 40 sorbitan arisoterate, flavor, dosium saccharin, and FD&C Blue No. 1.

It will be appreciated that a variety of different disinfectants can be employed, including other electromagnetic wavelengths, and various chemical compositions. The disinfectant medium can be introduced prior to ablation, during ablation and/or after the ablation. It can be delivered continuously. The level of disinfection of the oral cavity is selectable as is the volume of the oral cavity that is disinfected. The degree of disinfection varies. Disinfection is provided to reduce infection of the ablated body structure.

Ablation source delivery device 12 may be least partially positioned in an interior of catheter 14. In one embodiment, ablation source delivery device 12 is advanced and retracted through a port 18 formed in an exterior surface of catheter 14. Ablation source delivery device advancement and retraction device 20 advances ablation source delivery device 12 out of catheter 14, into an interior of a body structure and can also provide a retraction of ablation source delivery device 12 from the interior of the body structure. Although the body structure can be any number of different structures, the body structure will hereafter be referred to as the tongue. Ablation source delivery device 12 pierce an exterior surface of the tongue and are directed to an interior region of the tongue. Sufficient ablation energy is delivered by ablation source 12 to the interior of the tongue to cause the tongue to become sufficiently ablated and debulked. Ablation source delivery device 12 can be a hollow structure that is, (i) adapted to deliver different chemicals to a selected tongue interior ablation site (for chemical ablation) (ii) deliver alcohol or other liquids or semi-liquids to achieve ablation as well as a variety of different infusion mediums, including but not limited to saline, chemotherapy and the like. Different modalities can be combined to achieved a desired ablation including but not limited to RF and chemotherapy, chemical and chemotherapy. Ablation source delivery device 12 may have a limited travel distance in the tongue. In one embodiment with RF electrodes, this is achieved with an insulation sleeve that is in a surrounding relationship to an exterior of an electrode. Other devices can include a structure located on ablation source delivery device 12 which limits their advancement, or a structure coupled to a catheter which limits the advancement of ablation source delivery devices 12, such as a stop and the like.

Ablation source delivery device 12 can include a central lumen for receiving a variety of fluids that can be introduced into the interior of the tongue, as well as a plurality of fluid delivery ports. In one embodiment, the disinfectant agent is introduced through ablation source delivery device 12 into the interior of the selected body structure. One suitable fluid is an electrolytic solution. Instead of direct contact with tissue and ablation source delivery source 12 for the delivery of ablation energy and/or ablative agent, a cooled electrolytic solution can be used to deliver the ablation energy and/or ablative agent to the tissue. The electrolytic solution may be cooled in the range of about 30 to 55 degrees C.

Catheter 14 includes a catheter tissue interface surface 22, a cooling medium inlet conduit 24 and a cooling medium exit conduit 26 extending through an interior of catheter 14. Ports 18 are formed in the exterior of catheter 14, and are preferably formed on catheter tissue interface surface 22. Ports 18 are isolated from a cooling medium flowing in inlet and outlet conduits 24 and 26. Cooling medium inlet and exit conduits 24 and 26 are configured to provide a cooled section of catheter tissue interface surface 22 of at least 1 to 2 cm². In one embodiment, the cooled section of catheter tissue interface surface 22 is at least equal to the cross-sectional diameter of the underlying zone of ablation. In another embodiment, the cooled section of catheter tissue interface surface 22 only provides cooling to an area associated with each deployed ablation source delivery device.

The size of the cooled section of catheter tissue interface surface 22 varies for each patient. The size is sufficient enough to minimize swelling of the tongue following the delivery of the ablation creation source. The reduction of swelling can be 50% or greater, 75% or greater, and 90% and greater. The amount of cooling provided is sufficient to enable the patient to return home shortly after the debulking procedure is performed, and not run the risk of choking on the tongue. It has been found that by providing a sufficient level of cooling over a relatively large area, the amount of ablation in an interior region of the tongue is enhanced. By providing a sufficiently large enough cooled section of catheter tissue interface surface 22, an adenomas response is minimized.

Figure 3:
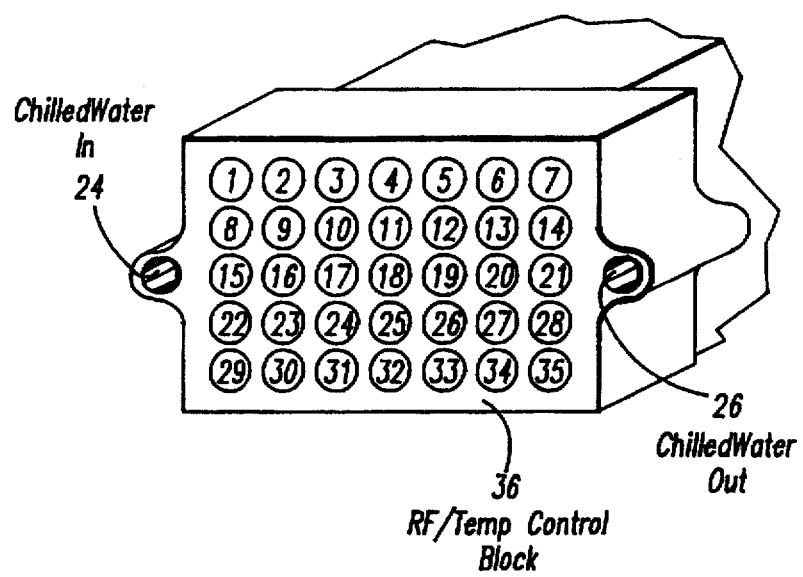
FIG. 3 is a perspective view of the connector illustrated in FIG. 1.
Figures 4, 5:
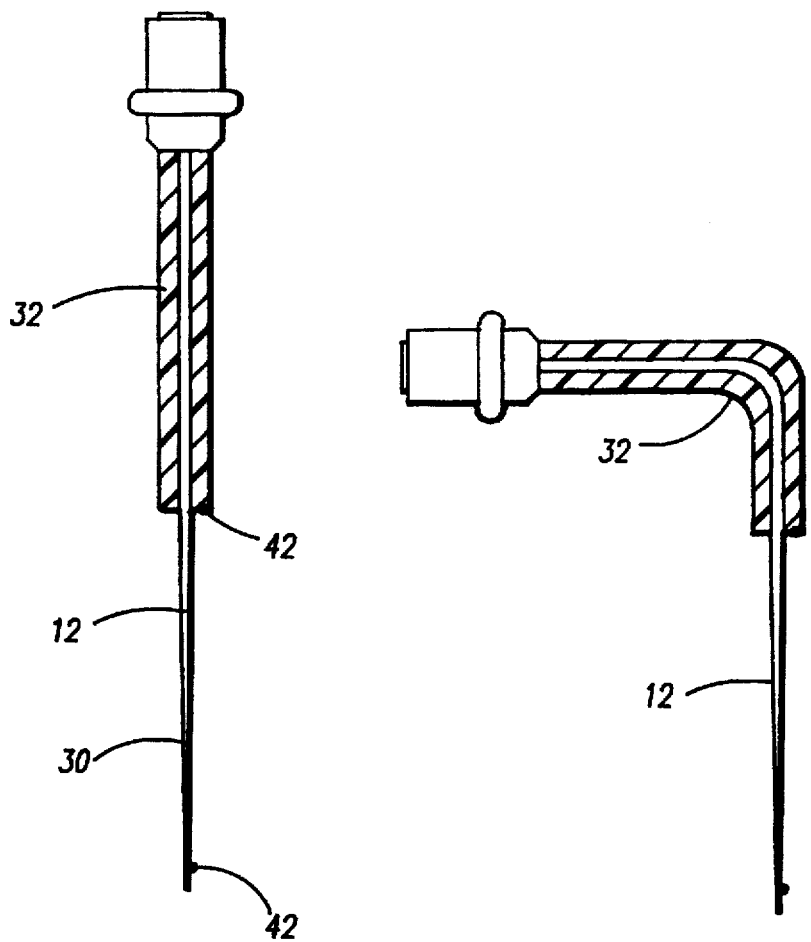
FIG. 4 is a perspective view of an ablation source delivery device associated with the debulking apparatus illustrated in FIG. 1.
FIG. 5 is a perspective view of a flexible ablation source delivery device utilized with the methods of the present invention.

An ablation delivery surface 30 of ablation source delivery device 12 can be adjusted by inclusion of an adjustable or non-adjustable insulation sleeve 32 (FIGS. 3, 4, and 5). Insulation sleeve 32 can be advanced and retracted along the exterior surface of ablation source delivery device 12 in order to increase or decrease the length of the ablation delivery surface 30. Insulation sleeve 32 can be made of a variety of materials including but not limited to nylon, polyimides, other thermoplastics and the like. The size of ablation delivery surface 30 can be varied by other methods including but not limited to creating a segmented ablation source delivery device 12 with a plurality of sections that are capable of being multiplexed and individually activated, and the like.

Referring specifically to FIG. 4, ablation source delivery device 12 has an advancement length 33 that extends from an exterior surface of catheter 14 and is directed into the interior of the tongue. Advancement length 33 is sufficient to position ablation delivery surface 30 at a selected tissue site in the interior of the tongue. Ablation delivery surface 30 is of sufficient length so that the ablation energy is delivered to the selected tissue site, create a desired level of ablation (cell necrosis) at the selected tissue site without causing damage to the hypoglossal nerve. Ablation delivery surface 30 is not always at the distal end of ablation source delivery device 12. Insulation 32 can also be positioned at the distal end of ablation source delivery device 12. In this embodiment, ablation delivery surface 30 does not extend to the distal end of ablation source delivery device 12. However, ablation delivery surface 30 still delivers sufficient ablation energy to create a desired level of cell necrosis in the interior of the tongue at the selected tissue site without damaging the hypoglossal nerve and/or damage to the surface of the tongue. Additionally, only one side or a portion of a side of ablation source delivery device 12 can be insulated. This also provides for an ablation source delivery device 12 which can be positioned throughout the tongue, including adjacent to a hypoglossal nerve. Where ablation source delivery device 12 is adjacent to the hypoglossal nerve, ablation source delivery device 12 is insulated.

In one embodiment, advancement length 33 is 1.2 to 1.5 cm, and the length of ablation delivery surface 30 is 5 to 10 mm, more preferably about 8 mm.

In another embodiment, advancement length 33 is insufficient to reach the hypoglossal nerve when introduced through any of the tongue surfaces, particularly the dorsum of the tongue.

Ablation source delivery device advancement device 20 is configured to advance at least a portion of each ablation source delivery device 12 to a placement position in the interior of the tongue. Ablation source delivery device advancement device 20 can also be configured to retract each ablation source delivery device 12. At the placement position, ablation delivery surface delivers sufficient ablation energy and/or effect to reduce a volume of the selected site without damaging a hypoglossal nerve and/or a surface of the tongue. In one embodiment, ablation source delivery device advancement and retraction device 20, with or without guide tracks 23, directs the delivery of ablation source delivery device 12 from catheter 14 into the interior of the tongue at an angle of 60 to 90 degrees relative to a longitudinal axis of catheter 14, and preferably about 70 degrees.

In certain embodiments, ablation source delivery device 12 has a geometric shape, including but not limited to a curved configuration that includes one or more insulated surfaces, either partially insulated on one side, at a proximal end, at a distal end, and the like, that is configured to reduce the volume of the selected tissue site without damaging a hypoglossal nerve. In one embodiment, ablation source delivery device 12 is introduced through any tongue surface and is configured so that a section of ablation source delivery device 12 which may be positioned close to the hypoglossal nerve is provided with insulation 32. As previously noted, insulation 32 can be positioned at different sites of ablation source delivery device 12.

Handle 16 is preferably made of an insulating material. Ablation source delivery device 12 may be made of a conductive material such as stainless steel. Additionally, ablation source delivery device 12 can be made of a shaped memory metal, such as nickel titanium, commercially available from Raychem Corporation, Menlo Park, Calif. In one embodiment, only a distal end of ablation source delivery device 12 is made of the shaped memory metal in order to effect a desired deflection. When introduced into the oral cavity, catheter 14 can be advanced until a patient's gag response is initiated. Catheter 14 is then retracted back to prevent patient's gagging. The distal end of ablation source delivery device 12 can be semi-curved. The distal end can have a geometry to conform to an exterior of the tongue.

In one embodiment of the invention catheter 14 is a handpiece and shall for purposes of this invention catheter 14 shall be referred to as ("handpiece 14"). In this embodiment, a separate handle 16 is not necessary. Debulking apparatus 10 is used to treat an interior region of the tongue. Handpiece 14 has a distal end that is sized to be positioned within an oral cavity. Ablation source delivery device 12 is at least partially positioned within an interior of handpiece 14. Ablation source delivery device 12 includes an ablation delivery surface 30. Ablation source delivery device advancement member 20 is coupled to ablation source delivery device 12 and calibrated to advance ablation source delivery device 12 from handpiece 20, including but not limited to a distal end of handpiece 20, into the interior of the tongue when handpiece 20 is positioned adjacent to a surface of the tongue. Ablation source delivery device 12 is advanced an advancement distance 33 from handpiece 20 of sufficient length to treat the interior region of the tongue with ablation energy and/or an ablative agent without damaging the hypoglossal nerve or the surface of the tongue.

Catheter 14 can be malleable in order to conform to the surface of the tongue when a selected ablation target site is selected. An encapsulated soft metal, such as copper, or an annealed metal/plastic material can be used to form malleable catheter 14. All or a portion of catheter 14 may be malleable or made of a shaped memory metal.

For many applications it is desirable for a distal end 14' of catheter 14 to be deflectable. This can be achieved mechanically or with the use of memory metals. A steering wire, or other mechanical structure, can be attached to either the exterior or interior of distal end 14'. In one embodiment, a deflection knob located on handle 16 is activated by the physician causing a steering wire to tighten. This imparts a retraction of distal end 14', resulting in its deflection. It will be appreciated that other mechanical devices can be used in place of the steering wire. The deflection may be desirable for tissue sites with difficult access.

Handle 6 can comprise a connector 34 coupled to retraction and advancement device 20. Connector 34 provides a coupling of a ablation source delivery device to power, feedback control, temperature and/or imaging systems. An RF/temperature control block 36 can be included.

In one embodiment, the physician moves retraction and advancement device 20 in a direction toward a distal end of connector 34. Ablation source delivery device 12 can be spring loaded. When ablation source delivery device advancement device 20 is moved back, springs cause selected ablation source delivery devices 12 to advance out of catheter 14.

One or more cables 38 may be coupled to ablation source delivery device 12 to an energy source 40. A variety of energy sources 40 can be used with the present invention to including but not limited to RF, microwave, ultrasound, coherent light, incoherent light, ultrasound, chemical ablation, alcohol ablation, thermal transfer, thermal jet, chemotherapy combined with RF, and other combinations of these sources. Preferably, energy source 40 is a RF generator. When a RF energy source is used, the physician can activate RF energy source 40 by the use of a foot switch (not shown) coupled to RF energy source 40.

One or more sensors 42 may be positioned on an interior or exterior surface of ablation source delivery device 12, insulation sleeve 32, or be independently inserted into the interior of the body structure. Sensors 42 permit accurate measurement of temperature at a tissue site in order to determine, (i) the extent of ablation, (ii) the amount of ablation, (iii) whether or not further ablation is needed, and (iv) the boundary or periphery of the ablated geometry. Further, sensors 42 prevent non-targeted tissue from being destroyed or ablated.

Sensors 42 are of conventional design, including but not limited to thermistors, thermocouples, resistive wires, and the like. Suitable sensors 42 include a T type thermocouple with copper constantene, J type, E type, K type, fiber optics, resistive wires, thermocouple IR detectors, and the like. It will be appreciated that sensors 42 need not be thermal sensors.

Sensors 42 measure temperature and/or impedance to permit ablation monitoring. This reduces damage to tissue surrounding the targeted ablation mass. By monitoring the temperature at various points within the interior of the body structure the periphery of ablation can be ascertained and it is possible to determine when the ablation is completed. If at any time sensor 42 determines that a desired ablation temperature is exceeded, then an appropriate feedback signal is received at energy source 40 and the amount of energy delivered is regulated.

Debulking apparatus 10 can include visualization capability including but not limited to a viewing scope, an expanded eyepiece, fiber optics, video imaging, and the like.

Additionally, ultrasound imaging can be used to position the ablation source delivery device 12 and/or determine the amount of ablation. One or more ultrasound transducers 44 can be positioned in or on ablation source delivery device 12, catheter 14, or on a separate device. An imaging probe may also be used internally or externally to the selected tissue site. A suitable imaging probe is Model 21362, manufactured and sold by Hewlett Packard Company. Each ultrasound transducer 44 is coupled to an ultrasound source (not shown).

Figure 6:
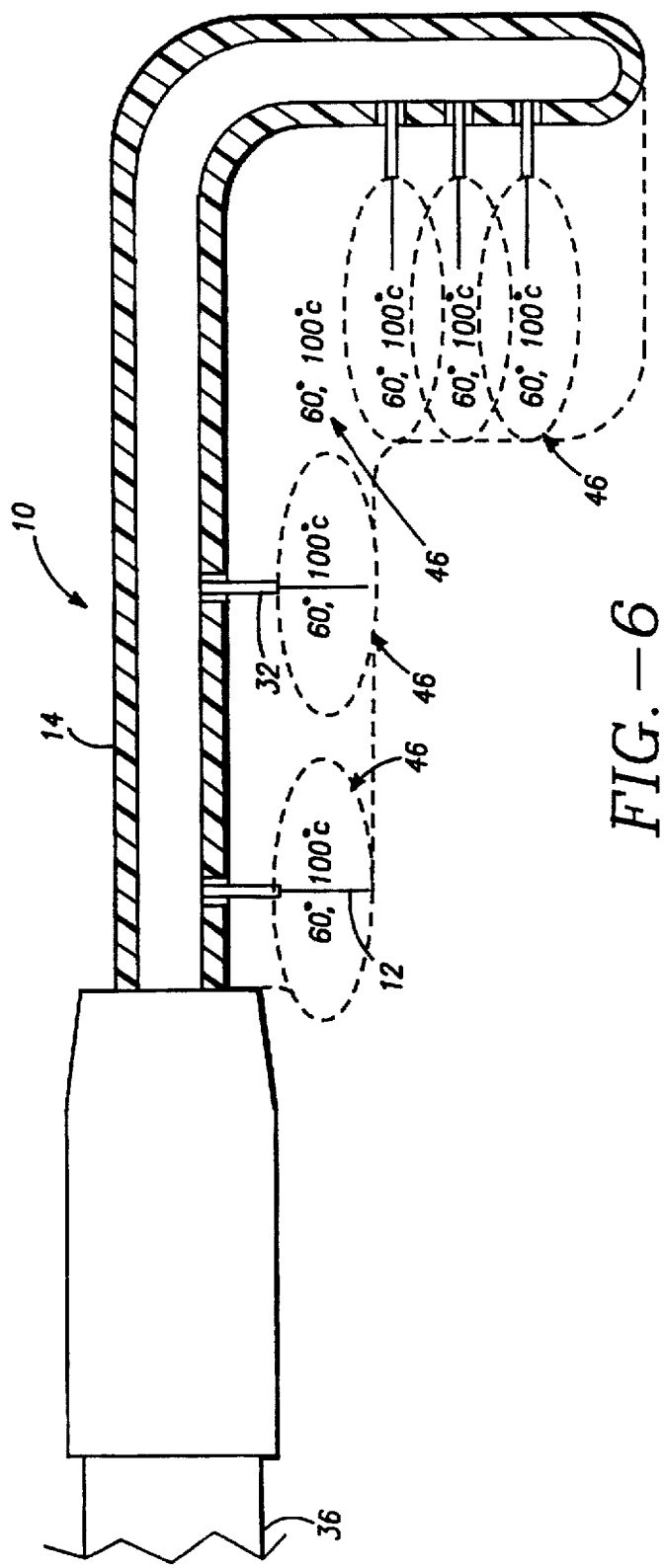
FIG. 6 illustrates the creation of ablation zones with the debulking apparatus shown in FIG. 1.
Figure 8:
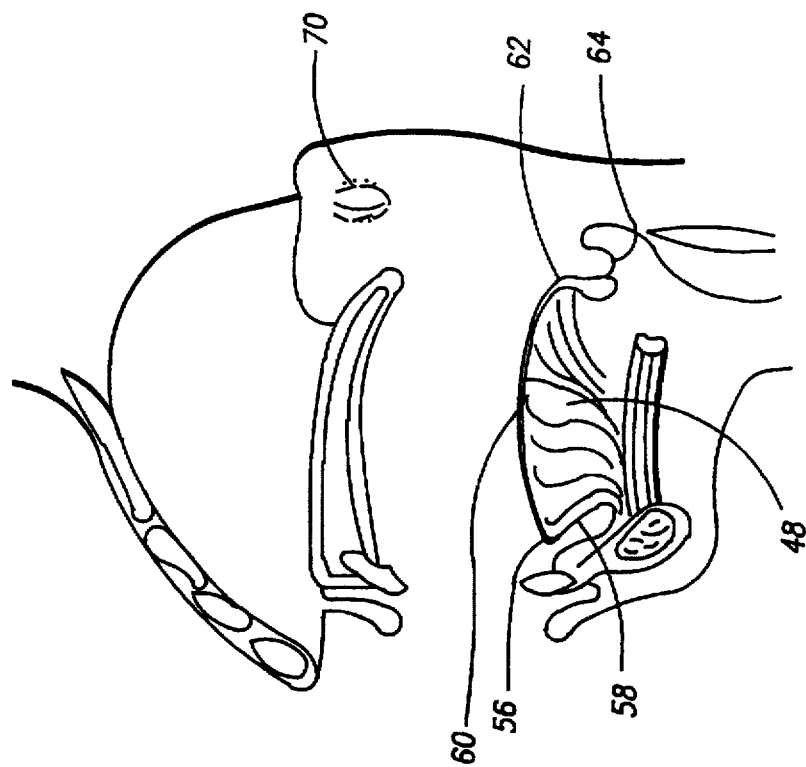
FIG. 8 is a cross-sectional view of the tongue with the mouth open.
Figure 7:
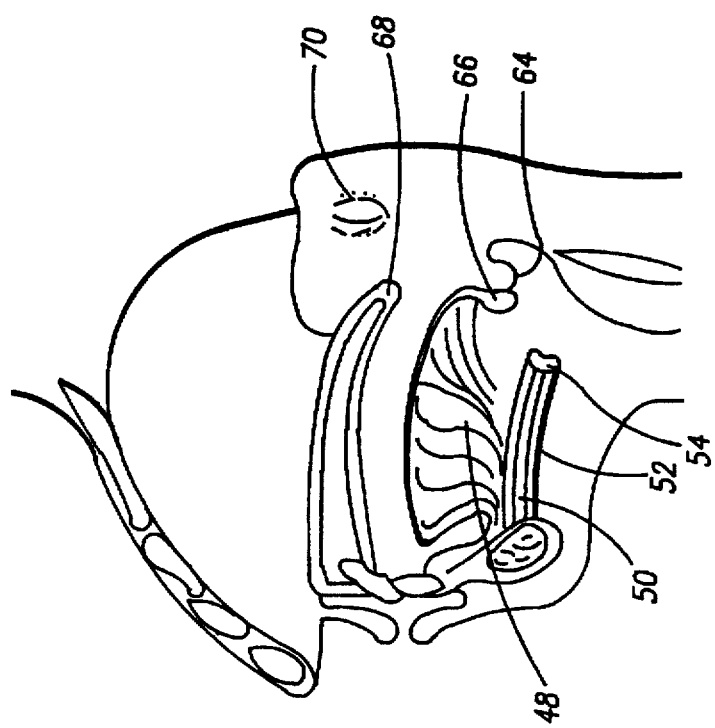
FIG. 7 is a cross-sectional view of the tongue with the mouth closed.
Figure 9:
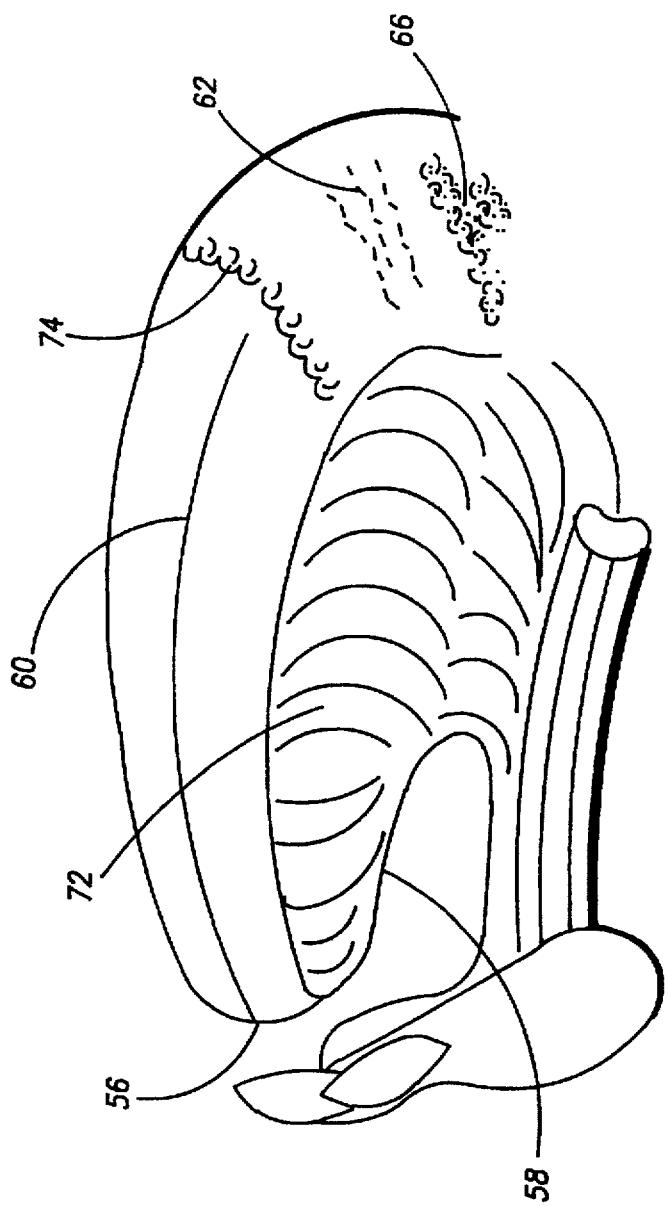
FIG. 9 is a perspective view of the tongue.
Figure 11:
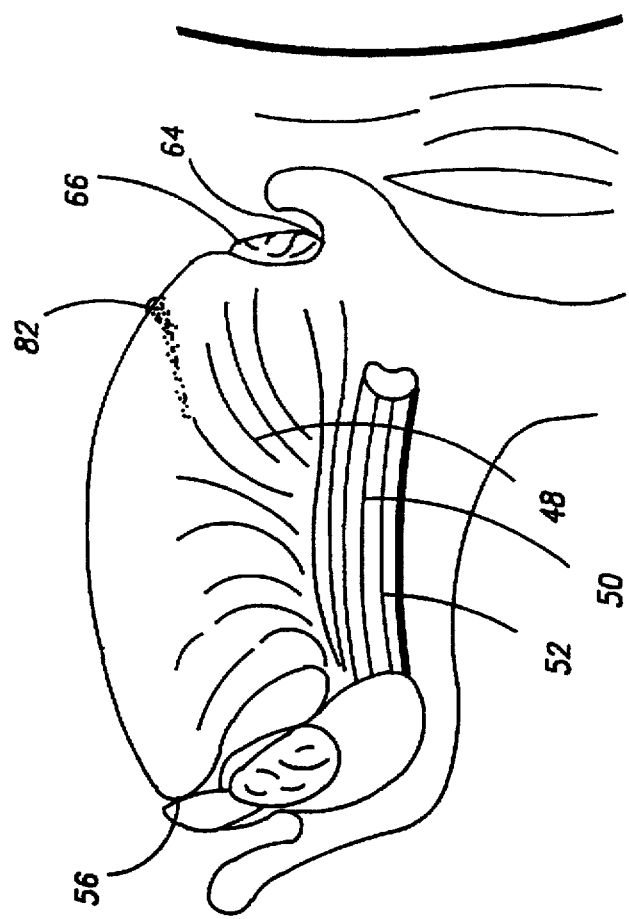
FIG. 11 is a cross-sectional view of the tongue.
Figure 10:
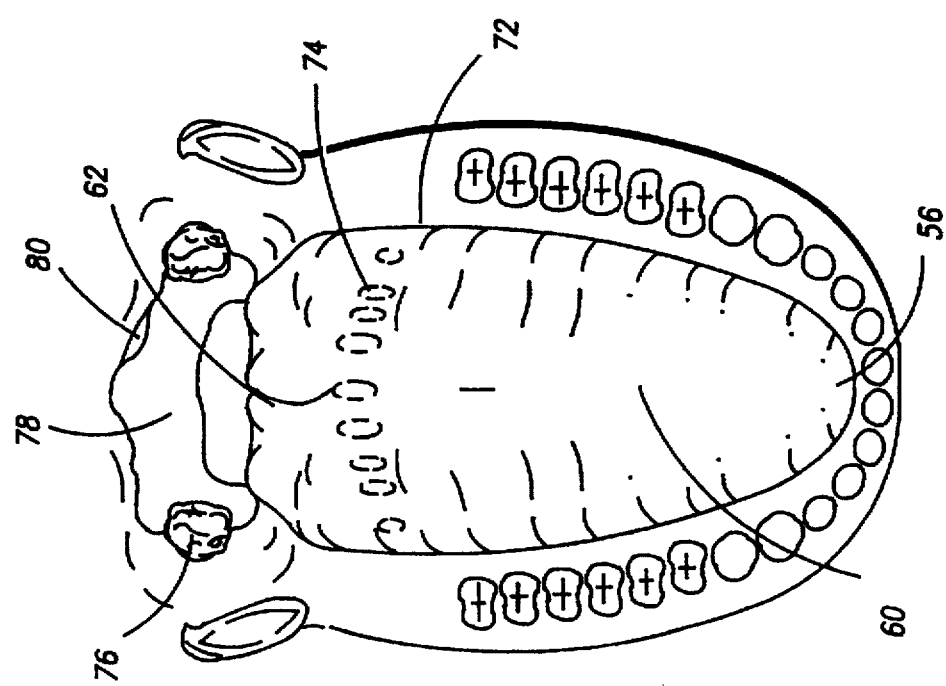
FIG. 10 is a perspective view of the dorsum of the tongue.
Figure 13:
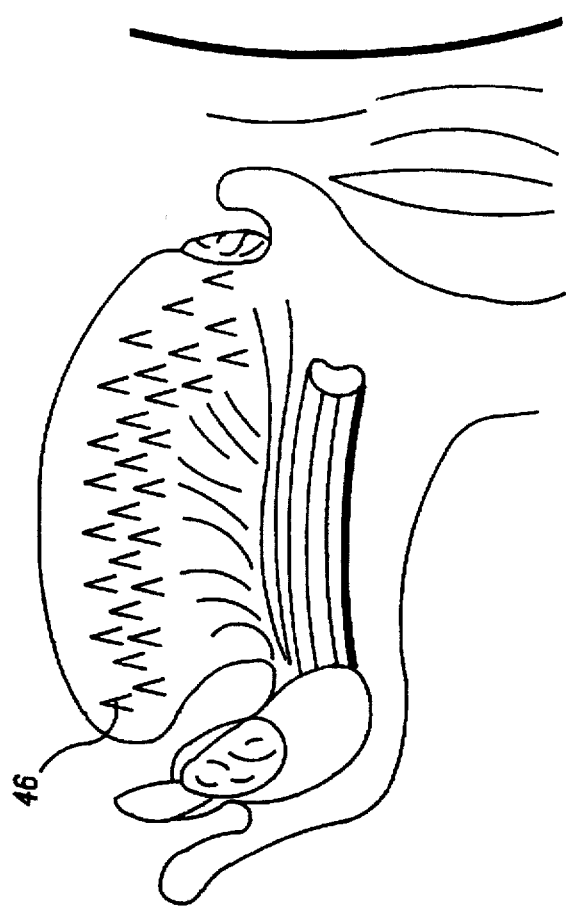
FIG. 13 is a cross-sectional view of the tongue illustrating a plurality of ablation zones.
Figure 12:
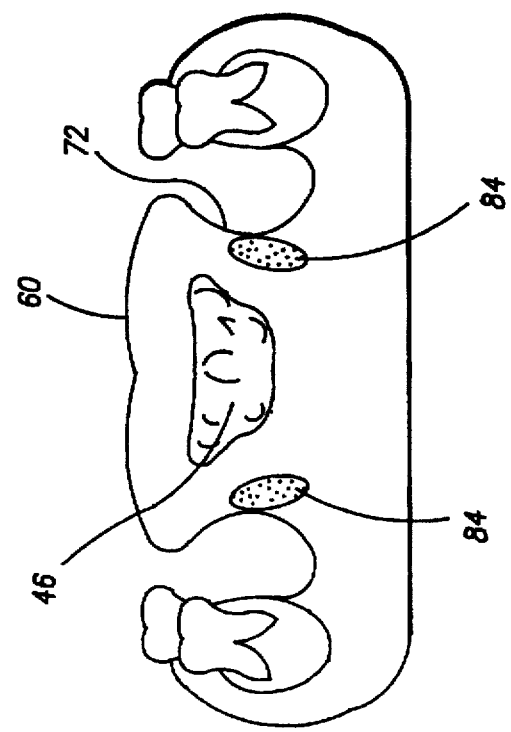
FIG. 12 is a cross-sectional view of the tongue illustrating the location of the hypoglossal nerves and the creation of an ablation zone.
Figure 15:
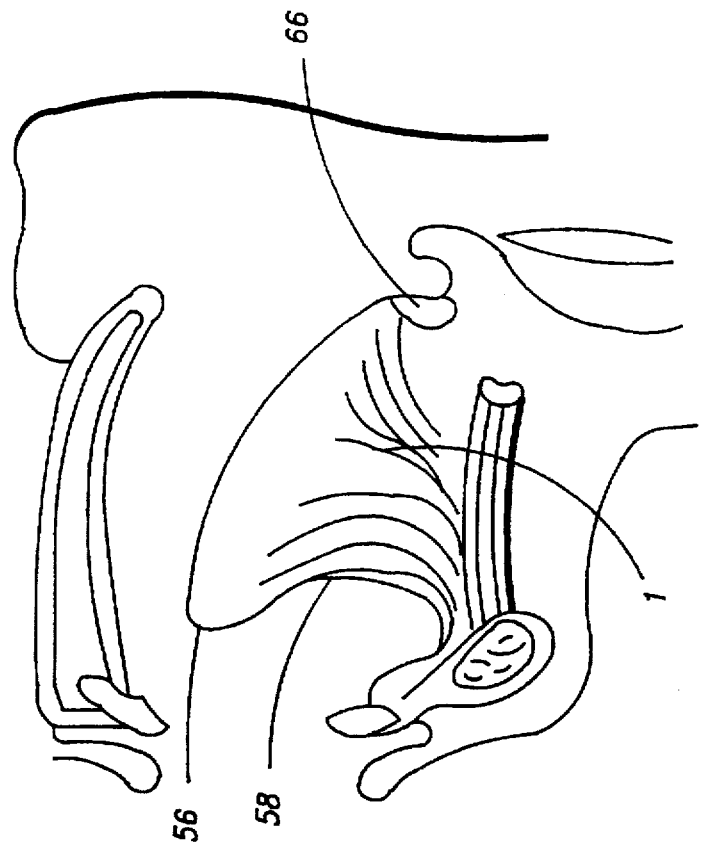
FIG. 15 is a cross-sectional view of the tongue.
Figure 14:
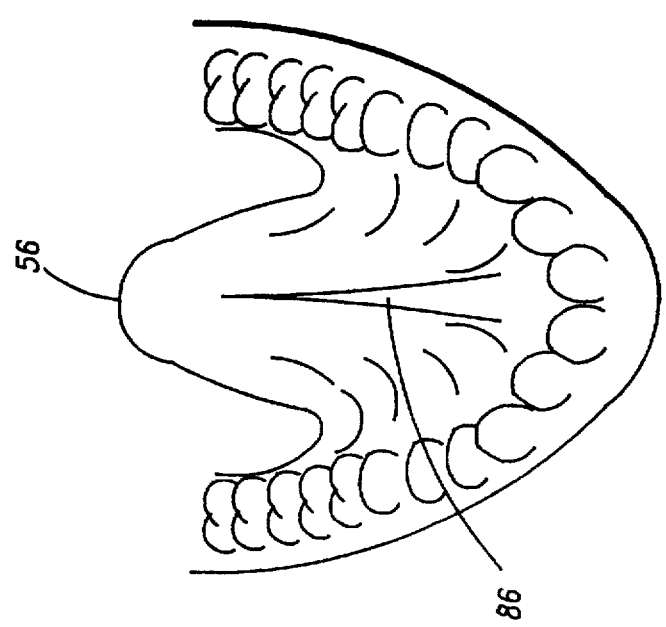
FIG. 14 is a perspective view of the ventral surface of the tongue.

With reference now to FIG. 6 catheter 14 is shown as being introduced into the oral cavity and multiple ablation source delivery devices 12 are advanced into the interior of the tongue creating different ablation zones 46. Using RF, Debulking apparatus 10 can be operated in either bipolar or monopolar modes. In FIG. 6, ablation source delivery device is an RF electrode operated in the bipolar mode, creating sufficient ablation zones 46 to debulk the tongue without affecting the hypoglossal nerves and creating a larger airway passage. With this debulking, the back of the tongue moves in a forward direction away from the air passageway. The result is an increase in the cross-sectional diameter of the air passageway.

Using RF, debulking apparatus 10 can also be operated in the monopolar mode. A groundpad can be positioned in a convenient place such as under the chin. In this embodiment, a single RF electrode is positioned in the tongue to create a first ablation zone 46. The RF electrode can then be retracted from the interior of the tongue, catheter 14 moved, and the RF electrode is then advanced from catheter 14 into another interior section of the tongue. A second ablation zone 46 is created. This procedure can be completed any number of times to form different ablation regions in the interior of the tongue.

More than one ablation source delivery device 12 can be introduced into the tongue and operated in the bipolar mode. One or more ablation source delivery devices 12 are then repositioned in the interior of the tongue any number of times to create a plurality of connecting or non-connecting ablation zones 46.

Referring now to FIGS. 7 through 15, various anatomical views of the tongue and other structures are illustrated. The different anatomical structures are as follows: the genioglossus muscle, or body of the tongue is denoted as 48; the geniohyoid muscle is 50; the mylohyoid muscle is 52; the hyoid bone is 54; the tip of the tongue is 56; the ventral surface of the tongue is denoted as 58; the dorsum of the tongue is denoted as 60; the inferior dorsal of the tongue is denoted as 62; the reflex of the vallecula is 64; the lingual follicles are denoted as 66; the uvula is 68; the adenoid area is 70; the lateral border of the tongue is 72; the circumvallate papilla is 74, the palatine tonsil is 76; the pharynx is 78; the redundant pharyngeal tissue is 80; the foramen cecum is 82; the hypoglossal nerve is 84, and the lingual frenum of the tongue is 86.

Dorsum 60 is divided into an anterior 2/3 and inferior dorsal 62. The delineation is determined by circumvallate papilla 74 and foramen cecum 82. Inferior dorsal 62 is the dorsal surface inferior to circumvallate papilla 74 and superior reflex of the vallecula 64. Reflex of the vallecula 64 is the deepest portion of the surface of the tongue contiguous with the epiglottis. Lingual follicles 66 comprise the lingual tonsil.

Catheter 14 can be introduced through the nose or through the oral cavity. Ablation source delivery device 12 can be inserted into an interior of the tongue through dorsum surface 60, inferior dorsal surface 62, ventral surface 58, tip 56 or geniohyoid muscle 50. Additionally, ablation source delivery device 12 may be introduced into an interior of lingual follicles 66 and into adenoid area 70. Once ablation source delivery device 12 is positioned, insulation sleeve 32, if included, may be adjusted to provided a desired energy delivery surface 30 for each ablation source delivery device 12.

Ablation zones 46 are created without damaging hypoglossal nerves 84. This creates a larger air way passage and provides a treatment for sleep apnea.

In all instances, the positioning of ablation source delivery device 12, as well as the creation of ablation zones 46 is such that hypoglossal nerves 84 are not ablated or damaged. The ability to swallow and speak is not impaired.

Figure 16:
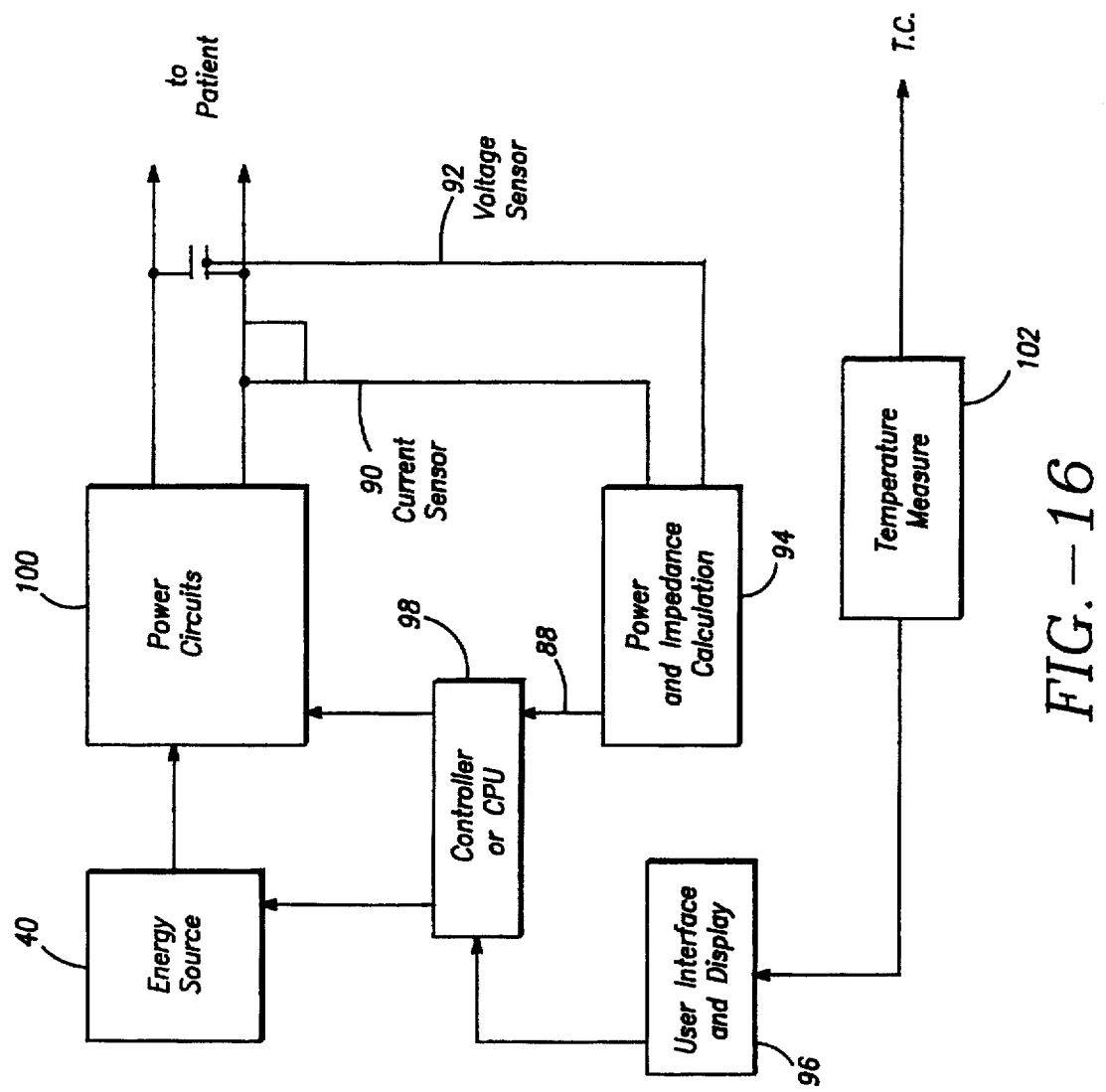
FIG. 16 is a block diagram of a feedback control system useful with the methods of the present invention.

FIG. 16 illustrates placement of ablation source delivery device 12 on the dorsum surface 60 of the tongue. The first ablation source delivery device 12 is positioned 0.5 cm proximal to the circumvallate papilla. The other ablation source delivery devices 12 are spaced 1.6 cm apart and are 1 cm off a central axis of the tongue. In one embodiment, 465 MHz RF was applied. The temperature at the distal end of ablation source delivery device 12 was about 100 degrees C. The temperature at the distal end of the insulation sleeve 32 was about 60 degrees C. In another embodiment, the temperature at the distal end of insulation sleeve 32 was 43 degrees C. and above. RF energy can be applied as short duration pulses with low frequency RF. Precise targeting of a desired ablation site is achieved. One or more ablation source delivery devices 12 may be used to create volumetric three-dimensional ablation. A variety of ablation geometries are possible, including but not limited to rectilinear, polyhedral, redetermined shapes, symmetrical and non-symmetrical.

Figure 17:
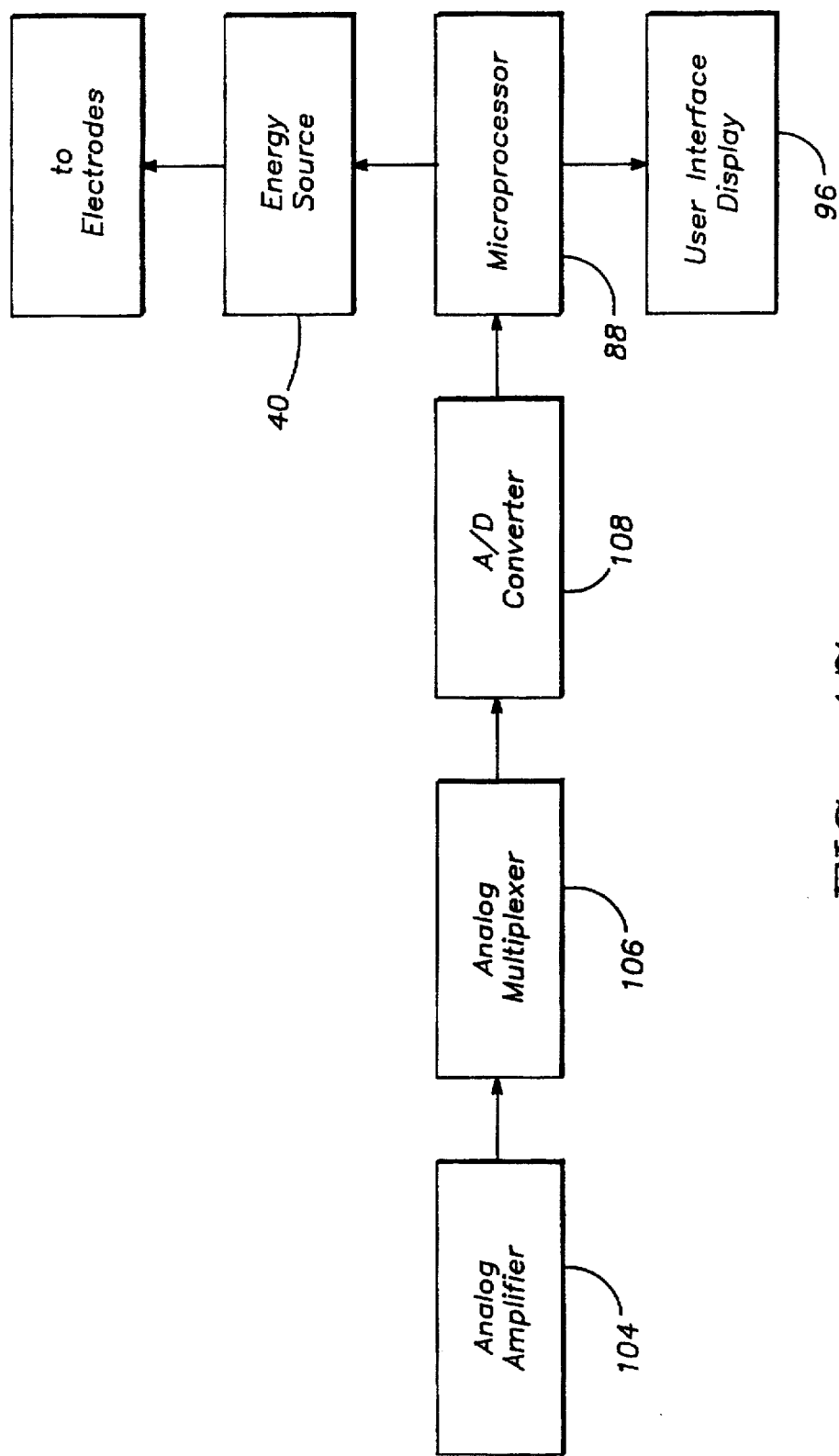
FIG. 17 is a block diagram illustrating an analog amplifier, analog multiplexer and microprocessor used with the feedback control system of FIG. 17.
Figure 18:
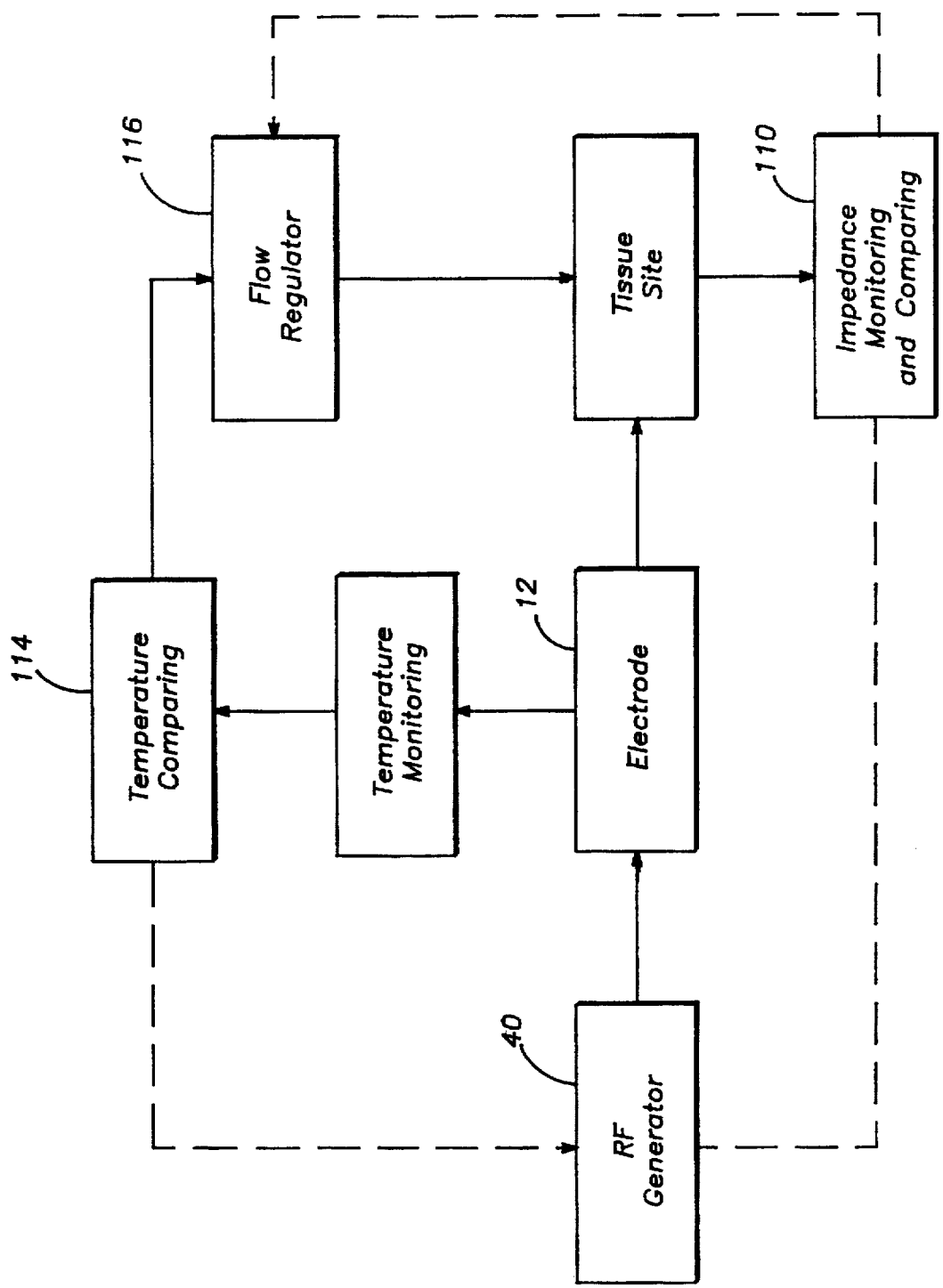
FIG. 18 is a block diagram of a temperature/impedance feedback system that can be used to control cooling medium flow rate through the catheter of FIG. 1.

Referring now to FIGS. 17 and 18 an open or closed loop feedback system couples sensors 42 to energy source 40. The temperature of the tissue, or of ablation source delivery device 12 is monitored, and the output power of energy source 40 adjusted accordingly. Additionally, the level of disinfection in the oral cavity can be monitored. The physician can, if desired, override the closed or open loop system. A microprocessor can be included and incorporated in the closed or open loop system to switch power on and off, as well as modulate the power. The closed loop system utilizes a microprocessor 88 to serve as a controller, watch the temperature, adjust the RF power, look at the result, refeed the result, and then modulate the power.

With the use of sensors 42 and the feedback control system a tissue adjacent to ablation source delivery device 12 can be maintained at a desired temperature for a selected period of time without impeding out. Each ablation source delivery device 20 may be connected to resources which generate an independent output for each ablation source delivery device. An output maintains a selected energy at ablation source delivery device 12 for a selected length of time.

When an RF electrode is used, current delivered through the RF electrode is measured by current sensor 90. Voltage is measured by voltage sensor 92. Impedance and power are then calculated at power and impedance calculation device 94. These values can then be displayed at user interface and display 96. Signals representative of power and impedance values are received by a controller 98. Signals representative of energy delivery for the different ablation sources can also be generated, measured and received by controller 98.

A control signal is generated by controller 98 that is proportional to the difference between an actual measured value, and a desired value. The control signal is used by power circuits 100 to adjust the power output in an appropriate amount in order to maintain the desired power delivered at respective ablation source delivery device 12.

In a similar manner, temperatures detected at sensors 42 provide feedback for maintaining a selected power. The actual temperatures are measured at temperature measurement device 102, and the temperatures are displayed at user interface and display 96. A control signal is generated by controller 98 that is proportional to the difference between an actual measured temperature, and a desired temperature. The control signal is used by power circuits 100 to adjust the power output in an appropriate amount in order to maintain the desired temperature delivered at the respective sensor. A multiplexer can be included to measure current, voltage and temperature, at the numerous sensors 42.

Controller 98 can be a digital or analog controller, or a computer with software. When controller 98 is a computer it can include a CPU coupled through a system bus. On this system can be a keyboard, a disk drive, or other non-volatile memory systems, a display, and other peripherals, as are known in the art. Also coupled to the bus is a program memory and a data memory.

User interface and display 96 includes operator controls and a display. Controller 98 can be coupled to imaging systems, including but not limited to ultrasound, CT scanners, X-ray, MRI, mammographic X-ray and the like. Further, direct visualization and tactile imaging can be utilized.

The output of current sensor 90 and voltage sensor 92 is used by controller 98 to maintain a selected power level at the RF electrodes. The amount of RF energy delivered controls the amount of power. A profile of power delivered can be incorporated in controller 98, and a preset amount of energy to be delivered can also be profiled. Other sensors similar to sensors 90 and 92 can be used by controller 98 for other ablation source delivery devices 12 to maintain a controllable amount of an ablation energy and/or ablative agent.

Circuitry, software and feedback to controller 98 result in process control, and the maintenance of the selected power that is independent of changes in voltage or current, and are used to change, (i) the selected power, (ii) the duty cycle (on-off and wattage), (iii) bipolar or monopolar energy delivery, and (iv) infusion medium delivery, including flow rate and pressure. These process variables are controlled and varied, while maintaining the desired delivery of power independent of changes in voltage or current, based on temperatures, or other suitable parameters, monitored at sensors 42.

Current sensor 90 and voltage sensor 92 are connected to the input of an analog amplifier 104. Analog amplifier 104 can be a conventional differential amplifier circuit for use with sensors 42. The output of analog amplifier 104 is sequentially connected by an analog multiplexer 106 to the input of A/D converter 108. The output of analog amplifier 104 is a voltage which represents the respective sensed temperatures. Digitized amplifier output voltages are supplied by A/D converter 108 to microprocessor 88. Microprocessor 88 may be a type 68HCII available from Motorola. However, it will be appreciated that any suitable microprocessor or general purpose digital or analog computer can be used to calculate impedance or temperature.

Microprocessor 88 sequentially receives and stores digital representations of impedance and temperature. Each digital value received by microprocessor 88 corresponds to different temperatures and impedances.

Calculated values, including but not limited to power and impedance, can be indicated on user interface and display 96. Alternatively, or in addition to the numerical indication of power or impedance, calculated impedance and power values can be compared by microprocessor 88 with power and impedance limits. When the values exceed predetermined power or impedance values, a warning can be given on user interface and display 96, and additionally, the delivery energy can be reduced, modified or interrupted. A control signal from microprocessor 88 can modify the power level supplied by energy source 40.

FIG. 18 illustrates a block diagram of a temperature/impedance feedback system that can be used to control cooling medium flow rate through catheter 14. Energy is delivered to ablation source delivery device 12 by energy source 44, and applied to tissue. A monitor 110 ascertains tissue impedance, based on the energy delivered to tissue, and compares the measured impedance value to a set value. If the measured impedance exceeds the set value a disabling signal 112 is transmitted to energy source 40, ceasing further delivery of energy to ablation source delivery device 12. If measured impedance, or other measured parameter, is within acceptable limits, energy continues to be applied to the tissue. During the application of energy to tissue sensor 42 measures the temperature of tissue and/or ablation source delivery device 12. A comparator 114 receives a signal representative of the measured temperature and compares this value to a pre-set signal representative of the desired temperature. Comparator 114 sends a signal to a flow regulator 116 representing a need for a higher cooling medium flow rate, if the tissue temperature is too high, or to maintain the flow rate if the temperature has not exceeded the desired temperature.

EXAMPLE 1

Debulking apparatus 10 was used to determine two-dimensional shrinkage of a bovine. RF volumetric reduction was achieved using a single needle electrode. Four mature ultrasonic crystals were positioned to form a square. Measurements were taken at control and post volumetric reduction at 15 watts initially with a 13% volumetric reduction, and 15 watts for 4 hours with an additional 4% volumetric reduction. A total 17% volumetric reduction was achieved.

EXAMPLE 2

Debulking apparatus 10 was used to determine three-dimensional shrinkage of a bovine tongue. RF volumetric reduction was achieved with a single needle electrode with eight miniature ultrasonic crystals, creating a cube. Application of 16 watts initially produced a 17% volumetric reduction of the tongue, 25 watts applied initially produced a 25% volumetric reduction, and 25 watts after hours produced an additional 4% reduction, for a total volumetric reduction of 29%.

EXAMPLE 3

A 35% volumetric reduction was achieved in porcine in vivo, with three dimensional gross at 20 watts initial application.

Figure 19:
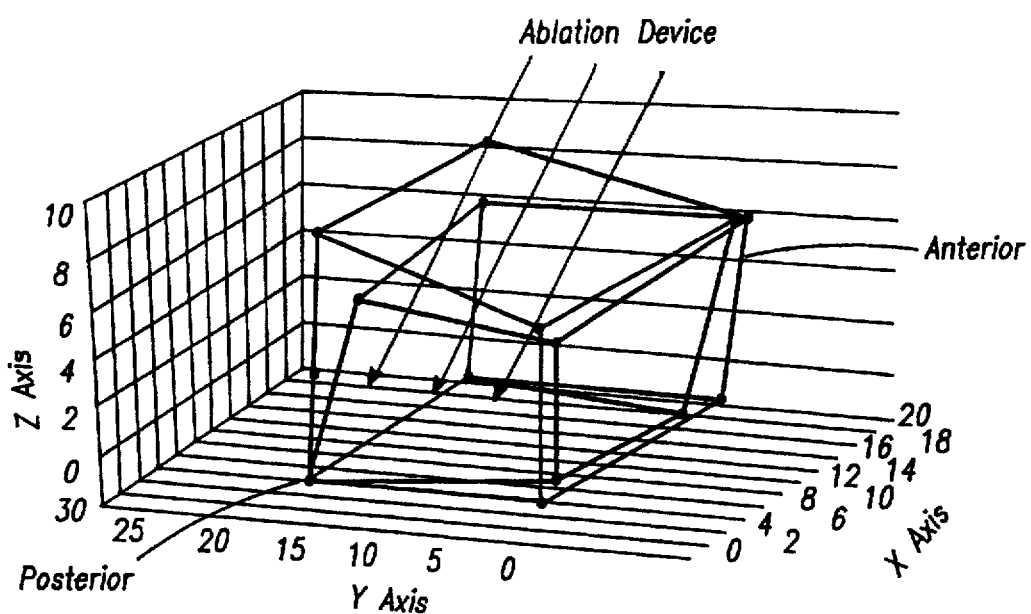
FIG. 19 is a three dimensional graph illustrating the percent shrinkage of the tongue following RF ablation.

Referring now to FIG. 19, ablation volume dimensions were measured with a multidimensional digital sonomicrometry. An average decrease in the Z direction was 20%, and volume shrinkage was 26%. Three-dimensional shrinkage of tongue tissue due to in vivo RF ablation with the needle, ablation with 20 Watts) is presented in FIG. 20. Control volume before ablation is compared with a post-ablation volume.

Figure 20:
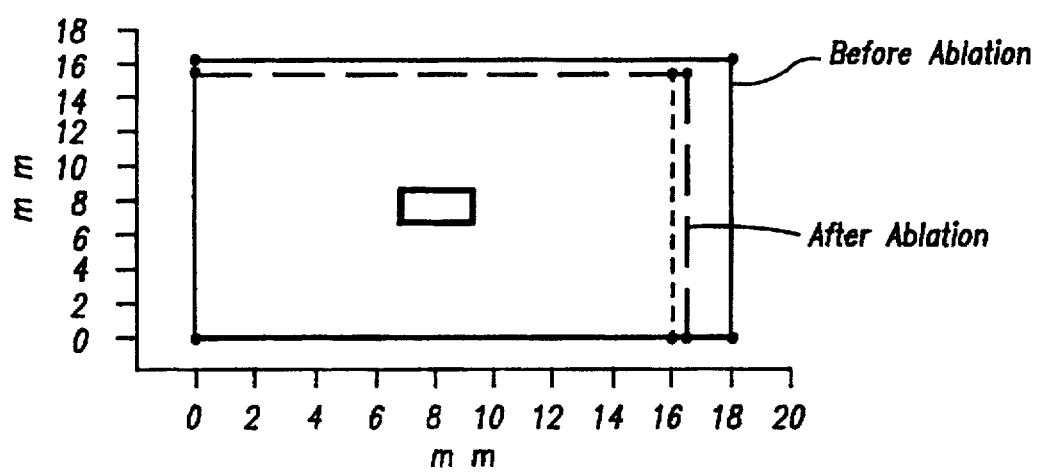
FIG. 20 is a graph illustrating two-dimensional shrinkage of bovine tongue tissue with RF ablation.

FIG. 20 illustrates two-dimensional shrinkage of a bovine tongue tissue due to RF ablation with a needle electrode. The before and after ablation results are illustrated.

Figure 21:
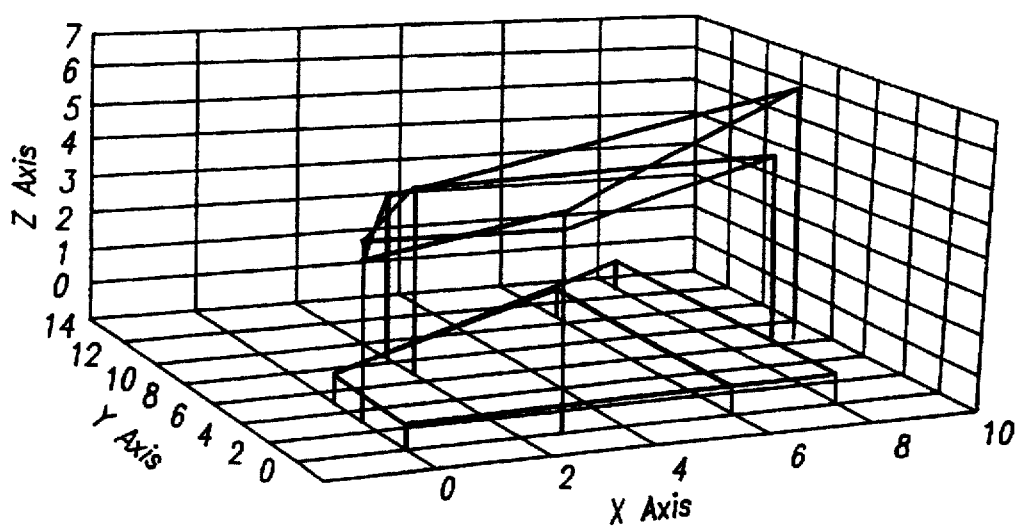
FIG. 21 is a graph illustrating three-dimensional shrinkage of bovine tongue tissue due to RF ablation.

FIG. 21 illustrates in graph form ablation at 16 Watts resulted in a 17% volume shrinkage of the tissue in post-ablation verses control. Ablation at 25 watts resulted in a 25% volume shrinkage after ablation. An additional 4% area shrinkage was obtained after in long-term post ablation (4 hours) verses post-ablation.

Figure 22:
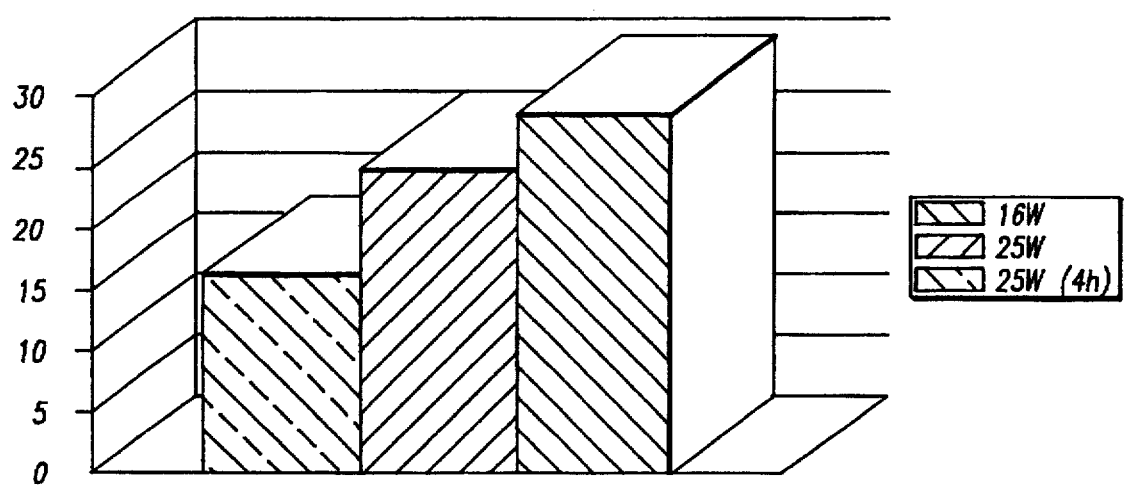
FIG. 22 is a graph illustrating percent volume change in a tongue following RF ablation.

FIG. 22 illustrates a percent volume change after RF ablation. 16 Watts, ablation at 16 Watts for 20 minutes; 25 Watts, ablation at 25 Watts for 20 minutes; 25 Watts (4 hours), and long tern post ablation (4 hours after 25 Watts ablation).

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A method for reducing a volume of a tongue, comprising:
   providing an ablation apparatus including a source of ablation energy and an ablation energy delivery device;
   advancing at least a portion of the ablation energy delivery device into an interior of the tongue;
   delivering a sufficient amount of energy from the energy delivery device into the interior of the tongue to debulk a section of the tongue without permanently damaging a main branch of a hypoglossal nerve; and
   retracting the ablation energy delivery device from the interior of the tongue.

2. The method of claim 1, wherein the energy source is an RF source and the ablation energy delivery device is an RF electrode.

3. The method of claim 1, wherein the energy source is a coherent source of light and the ablation energy delivery device is an optical fiber.

4. The method of claim 1, wherein the energy source is a heated fluid and the ablation energy delivery device is a catheter with a closed channel configured to receive the heated fluid.

5. The method of claim 1, wherein the energy source is a heated fluid and the ablation energy delivery device is a catheter with an open channel configured to receive the heated fluid.

6. The method of claim 1, wherein the energy source is a cooled fluid and the ablation energy delivery device is a catheter with a closed channel configured to receive the cooled fluid.

7. The method of claim 1, wherein the energy source is a cooled fluid and the ablation energy delivery device is a catheter with an open channel configured to receive the cooled fluid.

8. The method of claim 1, wherein the energy source is a cryogenic fluid.

9. The method of claim 1, wherein the energy source is a microwave source providing energy from 915 MHz to 2.45 GHz and the ablation energy delivery device is a microwave antenna.

10. The method of claim 1, wherein the energy source is an ultrasound source and the ablation energy delivery device is an ultrasound emitter.

11. The method of claim 1, wherein the energy source is a microwave source.

12. The method of claim 1, wherein the electrode is advanced into an interior of the tongue through a ventral surface of the tongue.

13. The method of claim 1, wherein the ablation energy delivery device is advanced into an interior of the tongue through an inferior dorsal surface of the tongue.

14. The method of claim 1, wherein the ablation energy delivery device is advanced into an interior of the tongue through a dorsum surface of the tongue.

15. The method of claim 1, wherein the ablation energy delivery device is advanced into an interior of the tongue through a tip of the tongue.

16. A method for reducing a volume of a tongue, comprising:
   providing an ablative agent source coupled to an ablative agent delivery device;
   advancing at least a portion of the ablative agent delivery device into an interior of the tongue;
   delivering a sufficient amount of an ablative agent from the ablative agent delivery device into the interior of the tongue to debulk a section of the tongue without permanently damaging a main branch of a hypoglossal nerve; and
   retracting the ablative agent delivery device from the interior of the tongue.

17. The method of claim 16, wherein the ablative agent is a chemical composition or mixture of compositions.

18. The method of claim 16, wherein the ablative agent includes an alcohol composition.

19. The method of claim 16, wherein the ablative agent is a chemotherapeutic agent.

20. The method of claim 19, further comprising:
   providing an RF electrode to deliver electromagnetic energy to an interior section of the tongue.

* * * * *